(12) United States Patent
Wakabayashi et al.

(10) Patent No.: US 7,153,290 B2
(45) Date of Patent: Dec. 26, 2006

(54) SYRINGE PUMP (75) Inventors: Keisuke Wakabayashi, Saitama (JP); Tatsuhiko Seki, Honjo (JP); Kazuo Matsubara, Bunkyo-ku (JP)

(73) Assignee: Atom Medical Corporation, Bunkyo-ku (JP)

( * ) Notice: Subject to any disclaimer, the term of this patent is extended or adjusted under 35 U.S.C. 154(b) by 222 days.

(21) Appl. No.: 10/633,162

(22) Filed: Jul. 30, 2003

(65) Prior Publication Data
US 2004/0057854 A1 Mar. 25, 2004

(30) Foreign Application Priority Data
Aug. 13, 2002 (JP) ............................. 2002-235767

(51) Int. Cl.
*A61M 37/00* (2006.01)
(52) U.S. Cl. ................................. 604/155; 128/DIG. 1
(58) Field of Classification Search ............. 604/93.01, 604/131, 154, 155, 187; 128/DIG. 1
See application file for complete search history.

(56) References Cited

U.S. PATENT DOCUMENTS 5,545,140 A * 8/1996 Conero et al. .............. 604/154
5,681,285 A * 10/1997 Ford et al. .................. 604/151
5,913,844 A * 6/1999 Ziemba et al. .............. 604/154
6,592,551 B1 * 7/2003 Cobb .......................... 604/155
2004/0073161 A1 * 4/2004 Tachibana .................... 604/67

* cited by examiner

*Primary Examiner*—Cris L. Rodriguez
*Assistant Examiner*—Mark K Han
(74) *Attorney, Agent, or Firm*—Ronald A. Sandler; Jones Day

(57) ABSTRACT

A flange attaching section has a flange supporting section and a movable section, and the movable section can approach the flange supporting section and separate therefrom due to rotational moving. Even if a flange section of a barrel of a syringe has various thickness, the flange section is easily attached between the flange supporting section and the movable section, and although the attachment is easy, the flange section comes in pressure contact with the flange supporting section in the attached state. Even if, therefore, the flange section of the barrel of the syringe has various thickness, a syringe pump, in which moving of the barrel of the syringe during infusion is prevented securely and the infusion is executed at an accurate speed, is provided.

3 Claims, 6 Drawing Sheets

SYRINGE PUMP

BACKGROUND OF THE INVENTION

1. Field of the Invention

The present invention relates to a syringe pump for injecting various drug solution, blood, or the like to human bodies using a syringe.

2. Description of the Related Art

Figure 1:
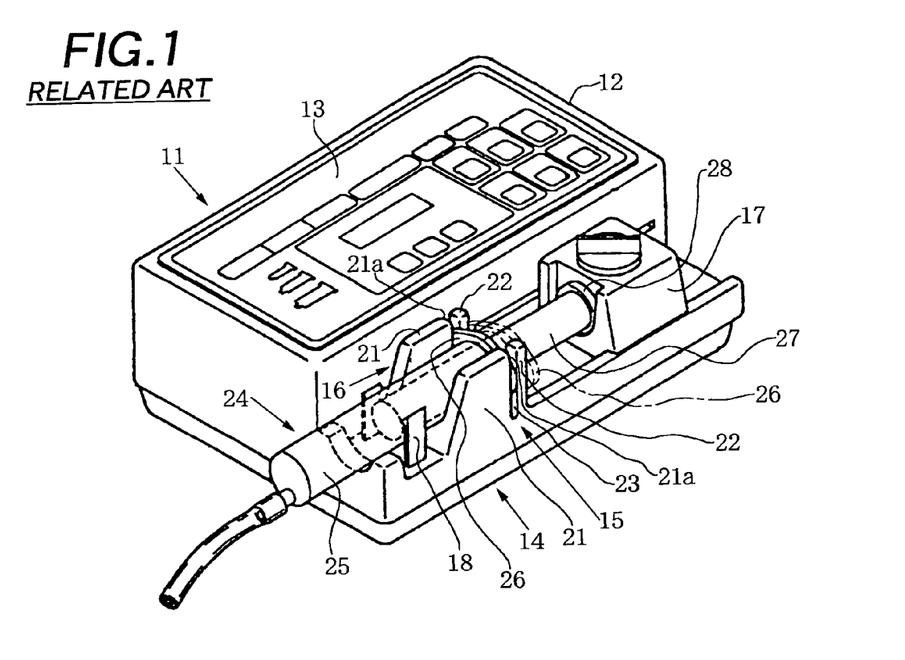
FIG. 1 is a perspective view that shows a first related art of the present invention in a state where a syringe is attached.

FIG. 1 shows a first related art of the syringe pump (JP, B2, 63-44389). The syringe pump 11 of the first related art includes an operation/display section 13 which is an upper surface portion of a case 12, and a syringe attaching section 14. The operation/display section 13 has various operation buttons and display sections, and the syringe attaching section 14 has a flange attaching section 15, a barrel attaching section 16, a slider 17 and a syringe diameter detecting section 18. The barrel attaching section 16 has a pair of projected ribs 21 which form a groove shaped section.

The flange attaching section 15 has end surfaces 21a of the pair of projected ribs 21 on a side of the slider 17, a pair of projected portions 22 opposed to the end surfaces 21a, and slits 23 between the end surfaces 21a and the projected portions 22. In order to use the syringe pump 11, the syringe 24 which is loaded with drug solution or the like is attached to the syringe attaching section 14. At the time of the attachment, a barrel 25 of the syringe 24 is attached to the barrel attaching section 16 and the syringe diameter detecting section 18, a flange section 26 of the barrel 25 is inserted into the slits 23, and a flange section 28 of a plunger 27 is attached to the slider 17.

The syringes 24 are manufactured by a plurality of manufacturers, and one manufacturer manufactures the syringes 24 of plural types. Dimensions of the respective sections of the syringe 24 differ according to manufacturers and types of the syringes 24, and a thickness of the flange section 26 of the barrel 25 also differs according to manufacturers and types of the syringes 24. Meanwhile, the syringe pump 11 is designed so as to be capable of being used for the syringes 24 of all manufacturers and all the types. A width of the slits 23 is, therefore, determined so that the most thick flange section 26 in the syringes 24 of various manufacturers and types can be inserted thereinto.

A diameter of the barrel 25 also differs according to manufacturers and types of the syringes 24. Since the syringe diameter detecting section 18, however, detects the diameter of the barrel 25, a sliding speed of the slider 17 for obtaining a desired infusion speed is determined based on the detected diameter. The slider 17 slides to a direction approaching the flange attaching section 15 at the determined sliding speed so as to press the flange section 28 of the plunger 27, and the plunger 27 is gradually inserted into the barrel 25. As a result, the infusion is executed always at the desired infusion speed regardless of the diameter of the barrel 25.

When the slider 17 slides to a position corresponding to a state where a tip of the plunger 27 is separated from the end surfaces 21a by a predetermined distance, a "warning that shows predetermined time before end of infusion" is given. When the slider 17 further slides to a position corresponding to a state where the tip of the plunger 27 is separated from the end surfaces 21a by a distance for reaching an injection end of the barrel 25, an "infusion end warning" is given. That is to say, an infusion quantity is calculated at the time of the infusion on the premise that the flange section 26 comes in pressure contact with the end surfaces 21a.

In a second related art of the syringe pump, an elastic supporting piece which elastically presses the flange section 26 of the barrel 25 of the syringe 24 against the end surfaces 21a is provided between the projected portions 22 in the syringe pump 11 of the first related art (JP, B2, 6-36827).

In the syringe pump 11 of the first related art, however, the width of the slits 23 is determined so that the flange section 26 which has the largest thickness in the syringes 24 of various manufacturers and types can be inserted thereinto. When the flange section 26 is inserted into the slits 23, therefore, a gap is normally generated between the slits 23 and the flange section 26.

When the slider 17 presses the plunger 27, the barrel 25 also moves to an opposite direction from the slider 17 in result until the flange section 26 comes in pressure contact with the end surfaces 21a. While the barrel 25 is moving, the infusion is not executed at all, or the infusion speed is lowered. Even if the moving distance of the barrel 25 is slight, when a slight quantity of highly medicable drug solution is infused or the like, the moving of the barrel 25 cannot be ignored.

On the contrary, in the syringe pump of the second related art, since the elastic supporting piece, which elastically presses the flange section 26 of the barrel 25 of the syringe 24 against the end surfaces 21a, is provided, when the flange section 26 is fitted between the elastic supporting piece and the end surfaces 21a, the flange section 26 comes in pressure contact with the end surfaces 21a. When the slider 17 presses the plunger 27, the barrel 25 does not move to the opposite direction from the slider 17.

In a state, however, in which the syringe 24 is attached to the syringe pump, since the plunger 27 of the syringe 24 is positioned above the elastic supporting piece, the elastic supporting piece should be necessarily shortened. Since the thin elastic supporting piece is easily damaged, the elastic supporting piece should be necessarily thicken, and in result it has strong elastic force. When the elastic supporting piece is short and has the strong elastic force, strong force should be applied to the elastic supporting piece in order to elastically deform it. In a state where the elastic supporting piece is not elastically deformed, the gap between the elastic supporting piece and the end surfaces 21a is extremely narrow.

The flange section 26 is, therefore, difficultly fitted between the elastic supporting piece and the end surfaces 21a, and even if the flange section 26 is not fitted therebetween, the flange section 26 is easily taken to be fitted by an operator. In the end, also in the syringe pump of the second related art, the barrel 25 frequently moves to the opposite direction from the slider 17 due to the pressing of the plunger 27 by the slider 17 until the flange section 26 comes in pressure contact with the end surfaces 21a.

In any one of the syringe pumps 11 of the first and second related arts, at the time of attaching the syringe 24, even if the flange section 26 of the barrel 25 is not attached into the slits 23 which is the proper position but is attached to an improper position, for example, a position which is closer to the slider 17 than the projected portions 22 as shown by a chain line in FIG. 1, the attachment to the improper position is not detected at all. When the flange section 26 of the barrel 25 is attached to the position which is closer to the slider 17 than the projected portions 22 as shown by the chain line in FIG. 1, the flange section 28 of the plunger 27 is separated from the end surfaces 21a excessively in comparison with the case where the flange section 26 is attached into the slits 23.

When the flange section 28 of the plunger 27 is attached to the slider 17, it is necessary to excessively separate also the slider 17 from the end surfaces 21a. The syringe pump 11 judges to necessarily infuse a larger quantity of the drug solution than the quantity of the drug solution with which the syringe 24 is actually loaded, namely, judges to necessarily slide the slider 17 over a longer distance than the proper distance, and starts the infusion. As a result, before the "infusion end warning" is given, or in some cases even before the "warning that shows predetermined time before end of infusion" is given, the tip of the plunger 27 reaches the injection end of the barrel 25.

Meanwhile, the tip portion of the plunger 27 has a flexible sealing member made of rubber or the like in order to seal the solution. When the pressing of the plunger 27 by the slider 17 is continued also after the tip of the plunger 27 reaches the injection end of the barrel 25, the sealing member on the tip of the plunger 27 is compressed so as to be deformed. That is to say, while the sealing member is being compressed and is deformed, the plunger 27 is continued to be pressed by the slider 17. Since, however, the compressive deformation of the sealing member is limited, when the plunger 27 cannot be moved despite the pressing of the plunger 27 by the slider 17, the syringe pump 11 judges that the syringe 24 is blocked, so that "blocking warning" is given.

During time when the tip of the plunger 27 reaches the injection end of the barrel 25 and then the "blocking warning" is given, however, the infusion is actually not executed at all. Even if, therefore, the syringe 24 is replaced immediately upon the "blocking warning", the infusion is regarded to be interrupted. When the infusion is interrupted while the solution is being infused in order to inject a slight quantity of vasopressor, hypotensor or the like, the interruption of the infusion is serious such that this determines life and death of a patient. Even when the interruption of the infusion is not so serious, the operator gets confused in the following case. The case is such that the infusion is actually completed before the "warning that shows predetermined time before end of infusion" or the "infusion end warning" is given, and that althougt the syringe 24 is not actually blocked, the "blocking warning" is given.

SUMMARY OF THE INVENTION

It is an object of the present invention to provide a syringe pump in which even if a flange section of a barrel of a syringe has various thickness, moving of the barrel of the syringe during infusion is prevented securely and the infusion is executed at an accurate speed, and when the flange section of the barrel of the syringe is not attached to a flange attaching section, this can be detected, and a quantity of solution is calculated accurately at the time of the infusion so that warning, display or the like is executed accurately.

In a syringe pump according to a first invention, a flange attaching section has a flange supporting section and a movable section, and the movable section can approach the flange supporting section and separate therefrom due to rotational moving. In the separation by the rotational moving, a gap between the flange supporting section and the movable section can be larger in comparison with separation by elastic deformation, for example. Even if the gap between the flange supporting section and the movable section is large in a state where the movable section is separated from the flange supporting section, at the time of approaching by the rotational moving, the gap between the flange supporting section and the movable section can be smaller in comparison with approaching by elastic deformation, for example.

Even if, therefore, the flange section of the barrel of the syringe has various thickness, the flange section is easily attached between the flange supporting section and the movable section. Although the attachment is easy, the flange section comes in pressure contact with the flange supporting section in the attached state. The moving of the barrel of the syringe during infusion is, therefore, prevented securely, the infusion is executed at an accurate speed. Further, a flange attaching operation section which rotationally moves the movable section of the flange attaching section is further provided separately from the flange attaching section. For this reason, even in such a case that an insufficient space is provided around the flange attaching section and thus an operator cannot easily and directly move the movable section rotationally, the flange section can be easily attached between the flange supporting section and the movable section.

In a preferred syringe pump according to the first invention, since barrel attaching section has not only a barrel supporting section but also a barrel pressing section, the moving of the barrel of the syringe during the infusion is prevented with high reliability. Since the flange attaching operation section serves also as the barrel pressing section, the moving of the barrel of the syringe during the infusion is prevented by a small number of operations, and omission of the operations for the prevention is less. Even if the flange section of the barrel of the syringe has various thickness, the infusion is executed at a more accurate speed and easily and securely.

In a syringe pump according to a second invention, after the movable section of the flange attaching section finishes approaching the flange supporting section, the barrel pressing section presses the barrel of the syringe against the barrel supporting section. The barrel is prevented from being pressed against the barrel supporting section in the state that the flange section does not come in pressure contact with the flange supporting section yet, the moving of the barrel of the syringe during the infusion is prevented with higher reliability. Even if, therefore, the flange section of the barrel of the syringe has various thickness, the infusion is executed at a more accurate speed.

In a syringe pump according to a third invention, a detecting section detects whether the flange section of the barrel of the syringe is attached to the flange attaching section or not. That is to say, when the flange section of the barrel of the syringe is not attached to the flange attaching section, the detecting section can detect this. For this reason, the operator can reattach the flange section to the flange attaching section immediately based on the detection by the detecting section. At the time of the infusion, therefore, an infusion quantity is calculated accurately, and warning, displaying, or the like is executed accurately.

DETAILED DESCRIPTION OF THE PREFERRED EMBODIMENT

The first embodiment of the present invention will be explained below with reference to FIGS. 2 through 9. FIGS. 6 through 9 show a syringe pump of the embodiment in a state where a syringe is not attached. The syringe pump 31 of the embodiment is provided with an operation/display section 33 which is an upper surface of a case 32, a handle section 34 and a syringe attaching section 35. The operation/display section 33 is provided with various operation buttons and display sections. The syringe attaching section 35 is provided with a flange attaching section 36, a barrel attaching section 37, a slider 38 and a syringe diameter detecting section 41.

A projected rib 42 which extends along a portion of the operation/display section 33 is provided on the barrel attaching section 37, and a groove 43 having a V-shaped section is provided between the operation/display section 33 and the projected rib 42. An end surface of the projected rib 42 on a side of the slider 38 is opposed to a projected portion 44 having a sectional shape similar to the projected rib 42, and a flange pressing plate 46 is opposed to an end surface 45 on a side of the slider 38 formed by the projected rib 42 and the operation/display section 33. The end surface 45, the flange pressing plate 46 and the like compose the flange attaching section 36. The flange pressing plate 46 has a section of V shape similar to the groove 43, and is mounted rotatively to the case 32 by a pair of pins 47a and 47b.

A flange pressing block 48 is mounted in the case 32 so as to be movable in an extending direction of the groove 43, and a groove 48a is provided on an end of the flange pressing block 48 on the side of the slider 38. A portion of the pin 47a which is projected from the flange pressing plate 46 is bent into an L shape, and its tip end is arranged in the groove 48a. A helical compression spring 51 is mounted to an end of the flange pressing block 48 opposite to the groove 48a, and the helical compression spring 51 applies energy to the flange pressing block 48 towards the groove 48a.

The groove 48a approaches the slider 38 by means of the moving of the flange pressing block 48 due to the applied energy. Since the tip of the pin 47a is arranged in the groove 48a, when the groove 48a approaches the slider 38, the pins 47a and 47b and the flange pressing plate 46 move rotationally, so that the tip of the flange pressing plate 46 comes in pressure contact with the end surface 45.

A cylinder section 52 whose outer peripheral surface is a plane within a predetermined angle range is provided between the projected rib 42 and the projected portion 44, and a knob 53, which has a cylindrical shape with an inner peripheral surface matching with the outer peripheral surface of the cylindrical section 52 and has a hook-shaped tip, wraps the cylindrical section 52. A cylindrical section 54 which is coaxially with the cylindrical section 52 is provided in the case 32, and the cylindrical section 54 is provided with a slit which extends to an axial direction. A pillar section 55 which is longer than the knob 53 is mounted to the knob 53 coaxially with the knob 53, and the pillar section 55 is projected into the case 32 via the cylindrical sections 52 and 54.

A cylindrical section 56, which has a rack 56a on an outer peripheral surface in the axial direction wraps the pillar section 55, and the rack 56a is inserted into the slit of the cylindrical section 54 in the axial direction. The cylindrical section 56 is prevented from dropping off from the pillar section 55 by an E ring 57 at the tip of the pillar section 55. A helical compression spring 58 wraps the pillar section 55 in the cylindrical sections 52 and 54, and the helical compression spring 58 applies energy to the cylindrical section 56, the pillar section 55 and the knob 53 in a direction from the outside to the inside of the case 32. In the states in FIGS. 6 through 9, a lower end surface of the knob 53 comes in pressure contact with an outer surface of the case 32.

A link fixture 61 is fitted into the outer peripheral surface of the cylinder section 56, and one end of a link 62 is mounted to the link fixture 61. The other end of the link 62 is mounted to the end of the flange pressing block 48 opposite to the groove 48a, and a plate section 48b extends from the end opposite to the groove 48a to a direction along the cylindrical section 54. A light emitting element 63 and a light receiving element are arranged on both sides of a tip of the plate section 48b. A potentiometer 64 is attached to a vicinity of the cylindrical section 54, and a gear of the potentiometer 64 is engaged with the rack 56a. The potentiometer 64, the rack 56a, the knob 53, and the like compose the syringe diameter detecting section 41.

The slider 38 is connected with a driving shaft 65 for sliding the slider 38, and a guide shaft 66 for guiding the slider 38 at the time of the sliding. The driving shaft 65 is connected with a driving mechanism in the case 32. The slider 38 includes a pair of holding sections 67 for holding the plunger of the syringe therebetween, a detecting section 68 for detecting the flange section of the plunger of the syringe, and an operation button 71 for operating the slider 38. When the operation button 71 is pressed, the holding sections 67 are separated from each other so as to be brought into a state where they can hold the plunger of the syringe therebetween, and the slider 38 is brought into a slidable state manually.

In order to use the above syringe pump 31, the knob 53 is moved on the outer peripheral surface of the cylindrical section 52 to a direction where it is separated from the outer surface of the case 32 against the applied energy of the helical compression spring 58. According to the moving, the pillar section 55 moves in the cylindrical sections 52 and 54 to a direction from the inside to the outside of the case 32. When the pillar section 55 is moved, the E ring 57 also moves simultaneously, and thus the cylindrical section 56 is also pushed by the E ring 57 so as to move in the cylindrical section 54 to the direction from the inside to the outside of the case 32.

Figure 5:
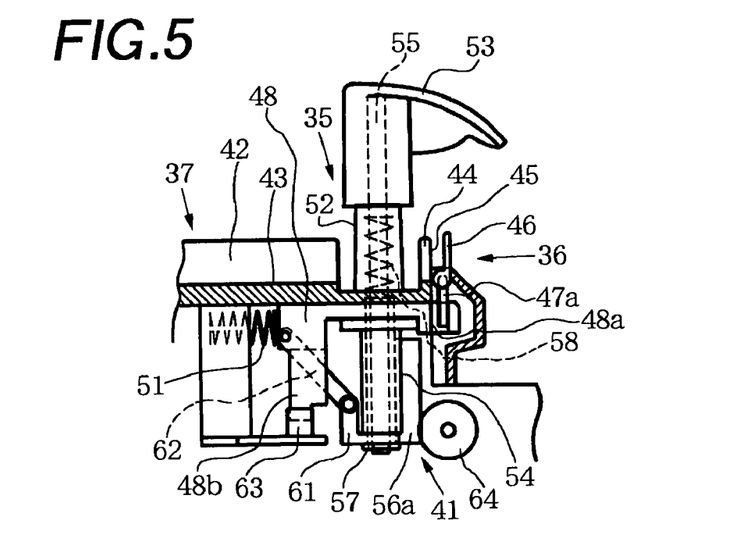
FIG. 5 is a sectional view that shows the main section in the first embodiment of the present invention in a preparation state for attaching the syringe.

At this time, the link fixture 61 receives the applied energy from the helical compression spring 51 via the link 62, and the applied energy of the helical compression spring 51 received via the link 62 includes a component directing from the outside to the inside of the case 32. The link fixture 61 slides with respect to the cylindrical section 56 due to the component, and does not approach the cylindrical section 54 until the E ring 57 touches the link fixture 61. When the knob 53 is further separated from the outer surface of the case 32 and the E ring 57 touches the link fixture 61, as shown in FIG. 5, the link fixture 61 is also pushed by the E ring 57 so as to move together with the cylindrical section 56 until it touches the cylindrical section 54.

When the link fixture 61 is pushed by the E ring 57, the flange pressing block 48 receives force from the link fixture 61 via the link 62. This force includes a component directing from the groove 48a of the flange pressing block 48 to the helical compression spring 51. Due to this component, the flange pressing block 48 is moved to a direction from the groove 48a to the helical compression spring 51 against the applied energy of the helical compression spring 51. Due to the moving of the flange pressing block 48, the pins 47a and 47b and the flange pressing plate 46 moves rotationally to a direction where the tip of the flange pressing plate 46 is separated from the end surface 45, so that a gap is formed between the end surface 45 and the flange pressing plate 46.

When the link fixture 61 touches the cylindrical section 54, the knob 53 can not be further separated from the outer surface of the case 32. In this state, a lower end surface of the knob 53 is slightly higher than an upper end surface of the cylindrical section 52, and the knob 53 and the pillar section 55 can be rotated with respect to the cylindrical section 52. As described above, the outer peripheral surface of the cylindrical section 52 is the plane within a predetermined angle range, and an inner peripheral surface of the knob 53 coincides with the outer peripheral surface of the cylindrical section 52. Therefore, when the knob 53 and the pillar section 55 are rotated with respect to the cylindrical section 52, a section of the knob 53 does not correspond to the section of the cylindrical section 52.

Figure 2:
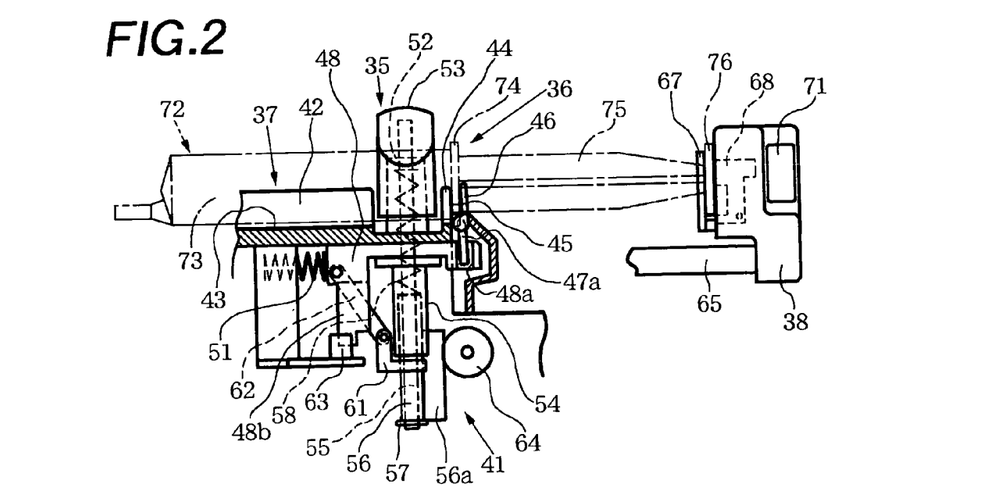
FIG. 2 is a sectional view that shows a main section in the first embodiment of the present invention in a state where the syringe is attached properly.
Figure 3:
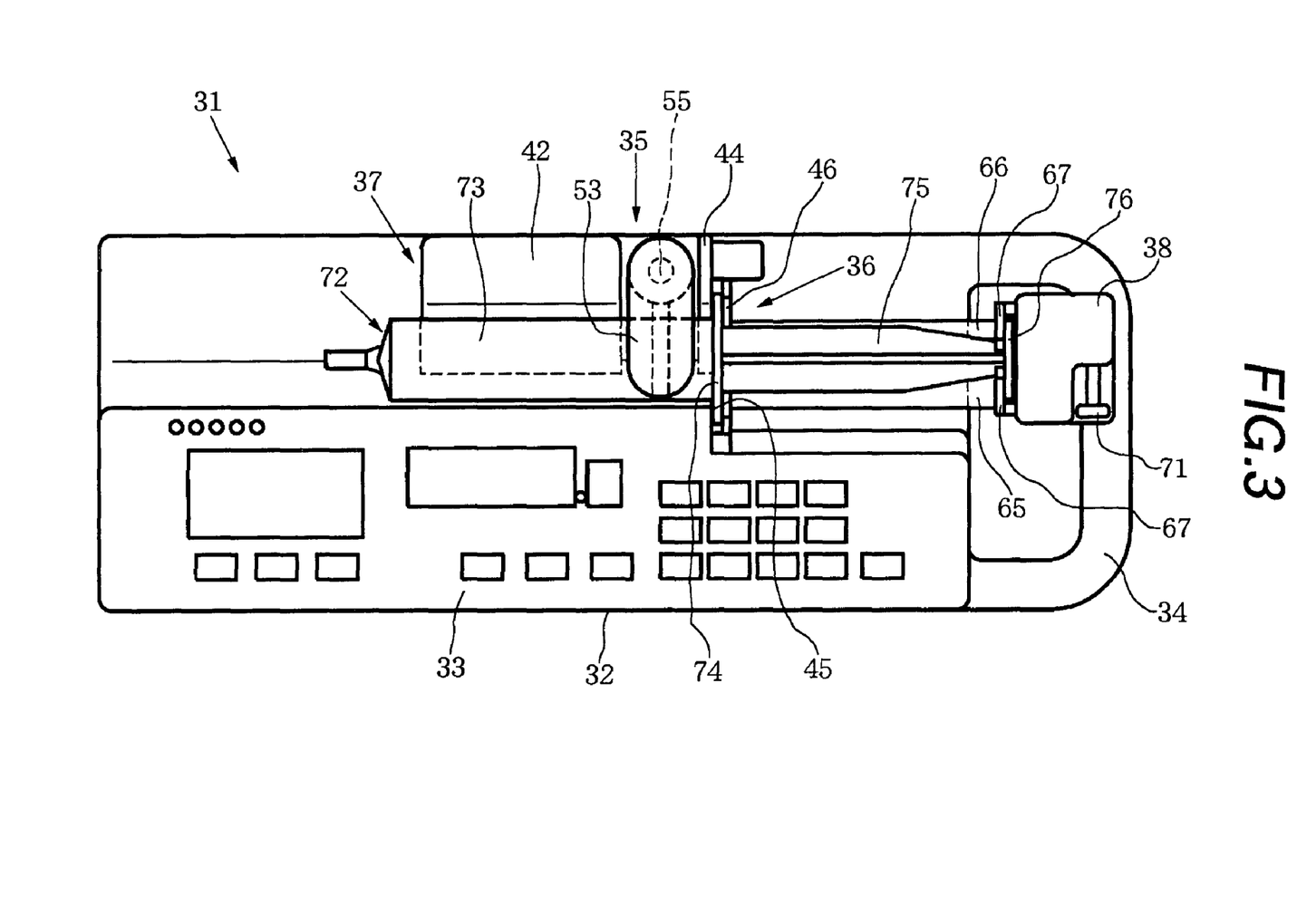
FIG. 3 is a plan view that shows the first embodiment of the present invention in the state where the syringe is attached properly.

Even if the force which separates the knob 53 from the outer surface of the case 32 against the applied energy of the helical compression spring 58 is released, in result, the knob 53 does not approach the outer surface of the case 32 in a state where it is positioned on the cylindrical section 52. In this state, therefore, as shown in FIGS. 2 and 3, a syringe 72 loaded with drug solution or the like is attached to the syringe attaching section 35. At the time of the attachment, a barrel 73 of the syringe 72 is attached to the barrel attaching section 37, and a flange section 74 of the barrel 73 is inserted into the gap formed between the end surface 45 and the flange pressing plate 46 in the state of FIG. 5. A width of the gap is determined so that even the flange section 74 with the largest thickness in the syringes 27 of various manufacturers and types can be inserted.

In a state where the operation button 71 is pressed and the holding sections 67 are separated from each other, a plunger 75 is slid manually to a position where the plunger 75 can be held between the holding sections 67. In this position, the pressing of the operation button 71 is released and the holding sections 67 approach each other so that the plunger 75 is held between the holding sections 67. The knob 53 and the pillar section 55 are, thereafter, rotated with respect to the cylindrical section 52 to a direction opposite to the rotation for obtaining the state in FIG. 5 until the section of the knob 53 corresponds to the section of the cylindrical section 52.

The knob 53, in result, moves on the outer peripheral surface of the cylindrical section 52 to a direction where the knob 53 approaches the outer surface of the case 32 due to the applied energy of the helical compression spring 58. According to the moving, the pillar section 55 moves in the cylindrical sections 52 and 54 to a direction from the outside to the inside of the case 32. When the pillar section 55 moves, the E ring 57 also moves simultaneously, and thus the cylindrical section 56 also moves in the cylindrical section 54 to the direction from the outside to the inside of the case 32 due to the applied energy of the helical compression spring 58.

When the E ring 57 moves simultaneously with the pillar section 55, the force, which is applied from the E ring 57 via the link fixture 61 and the link 62 to the flange pressing block 48, is released. As a result, the flange pressing block 48 moves towards the groove 48a by the applied energy of the helical compression spring 51, and the groove 48a approaches the slider 38. The pins 47a and 47b and the flange pressing plate 46, therefore, move rotationally to the direction where the flange pressing plate 46 approaches the end surface 45. The flange pressing plate 46 presses the flange section 74 and the flange section 74 comes in pressure contact with the end surface 45.

The link fixture 61 also moves together with the cylindrical section 56 by the applied energy from the helical compression spring 51 via the link 62 so as to be separated from the cylindrical section 54. When the flange section 74 comes in pressure contact with the end surface 45, the flange pressing block 48 and the link fixture 61 do not move any more. Also after the flange section 74 comes in pressure contact with the end surface 45, the knob 53 approaches the outer surface of the case 32. The knob 53, however, presses the barrel 73 of the syringe 72, and when the barrel 73 comes in pressure contact with the inner surface of the groove 43, the knob 53 does not move any more.

As sown in FIG. 2, when the flange pressing plate 46 presses the flange section 74 and the flange section 74 comes in pressure contact with the end surface 45, even if the thickness of the flange section 74 is the smallest in the syringes 72 of various manufacturers and types, the tip of the plate section 48b of the flange pressing block 48 is positioned between the light emitting element 63 and the light receiving element. The light receiving element cannot, therefore, receive light from the light emitting element 63, and in result a detection is made that the flange section 74 is attached properly to the flange attaching section 36. In this detecting state, the infusion can be started normally.

When the flange section 74 comes in pressure contact with the end surface 45, even if the flange section 74 has various thickness, the moving of the barrel 73 due to the the pressing of the flange section 76 of the plunger 75 by the slider 38 during the infusion can be prevented. The infusion is, therefore, executed at an accurate speed.

Figure 4:
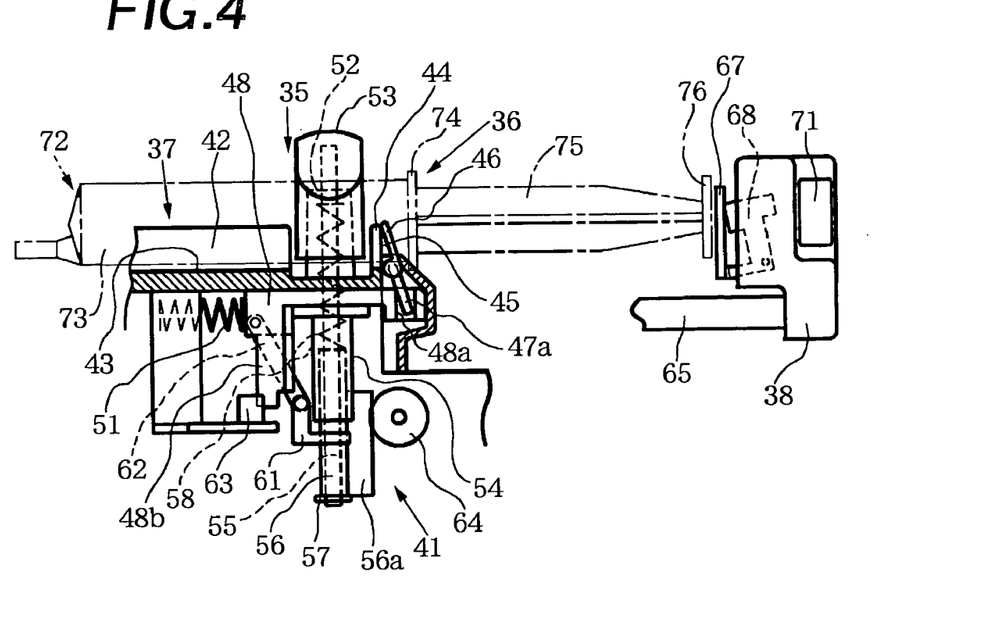
FIG. 4 is a sectional view that shows the main section in the first embodiment of the present invention in a state where the syringe is attached improperly.
Figure 6:
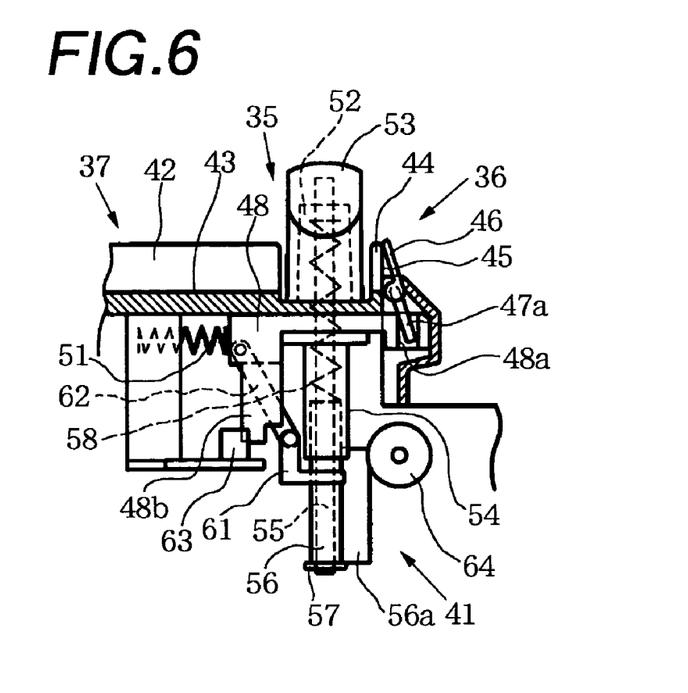
FIG. 6 is a sectional view that shows the main section in the first embodiment of the present invention in a state where the syringe is not attached.
Figure 7:
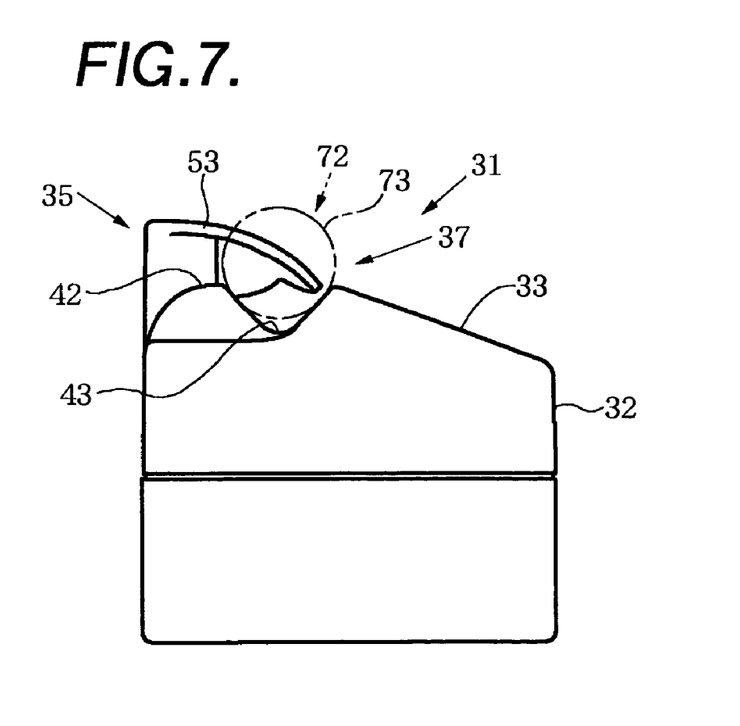
FIG. 7 is a side view that viewed from a position of line VII—VII in FIG. 9.
Figure 8:
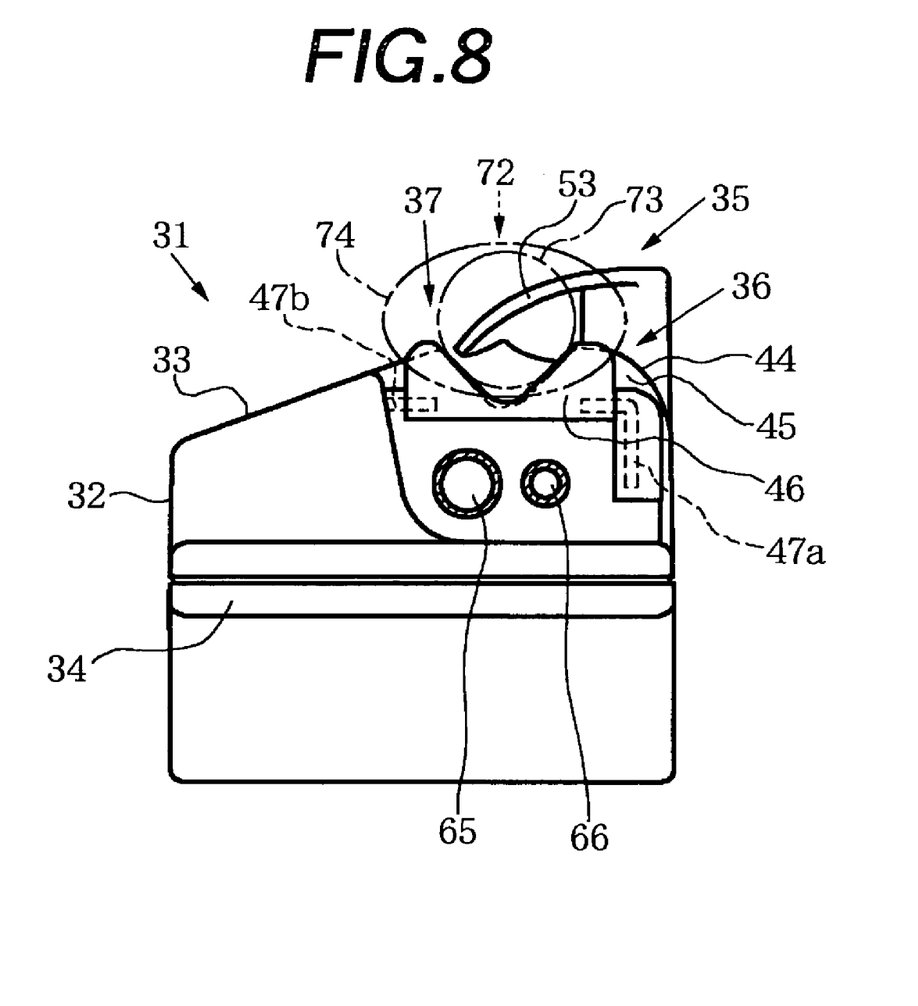
FIG. 8 is a sectional view that viewed from a position of line VIII—VIII in FIG. 9.
Figure 9:
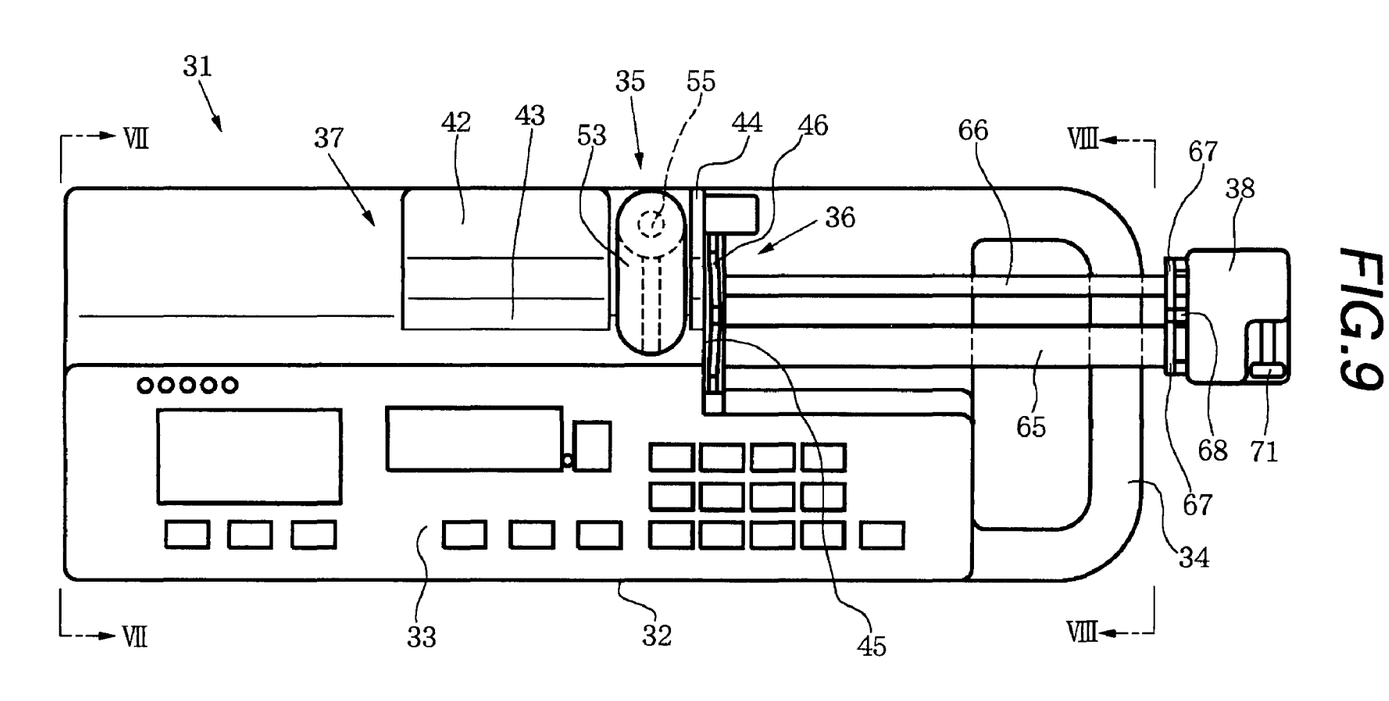
FIG. 9 is a plan view that shows the first embodiment of the present invention in the state where the syringe is not attached.

Meanwhile, when the syringe 72 is not attached to the syringe pump 31 at all as shown in FIG. 6, or the barrel 73 of the syringe 72 is attached to the barrel attaching section 37 but the flange section 74 is not attached to the flange attaching section 36 as shown in FIG. 4, the tip of the plate section 48b is not in a position where the light receiving element can be inhibited from receiving the light from the light emitting element 63. The detection is made by the light receiving that the flange section 74 is not attached to the flange attaching section 36. In this detecting state, if the infusion is tried to be started, the operation/display section 33 warns and displays this, and thus the infusion cannot be started.

Also in the case where the plunger 75 of the syringe 72 is not held between the holding sections 67 as shown in FIG. 4, this is detected by the detecting section 68. The operation/display section 33 warns and displays this, and thus the infusion cannot be started. An operator can, therefore, reattach the syringe 72 to the syringe attaching section 35 and the slider 38 based on the warning and the displaying.

When the syringe 72 is attached to the syringe attaching section 35 properly, the knob 53 is still in a state where it presses the barrel 73, and the engaged position between the gear of the potentiometer 64 and the rack 56*a* corresponds to a diameter of the barrel 73. The diameter of the barrel 73 is, therefore, obtained from an output of the potentiometer 64. When the diameter has a nonstandard value, the operation/display section 33 warns and displays this, and thus the infusion cannot be started. When the diameter of the barrel 73 has a standard value, a sliding speed of the slider 38 for obtaining a desired infusion speed is determined from the diameter.

In order to detach the syringe 72 from the syringe attaching section 35 when the infusion is ended and the syringe 72 is tried to be replaced by new one during the infusion, the knob 53 is changed from the state of FIG. 2 into the state of FIG. 5 in a similar manner to that when the knob 53 is changed from the state of FIG. 6 into the state of FIG. 5 so that the syringe 72 is attached. In this case, after the knob 53 releases the pressing against the barrel 73, the flange pressing plate 46 moves rotationally to the direction where it is separated from the end surface 45. As is clear from the above explanation, the knob 53 serves also as an operating unit for making the flange pressing plate 46 approximate to the end surface 45 and separating them, and a pressing unit for pressing the barrel 73.

The knob 53 does not necessarily serve also as the operating unit and the pressing unit, and the operating unit for making the flange pressing plate 46 approximate to the end surface 45 and separating them may be provided separately from the knob 53. The force, which moves rotationally the pins 47*a* and 47*b* and the flange pressing plate 46 to the direction where the flange pressing plate 46 approaches the end surface 45, is obtained by the helical compression spring 51, but the force may be obtained by another unit such as an eccentric cam.

The invention claimed is:

1. A syringe pump, comprising:
a flange attaching section having a flange supporting section and a movable section, the flange supporting section for contacting a flange section of a barrel of a syringe so as to support the flange section, the movable section being adjustable around a rotational axis extending generally parallel to the flange supporting section, whereby the flange section of the syringe barrel is locatable between the flange supporting section and the movable section; and
a flange attaching operation section for causing rotation of the movable section.

2. The syringe pump according to claim 1, further comprising:
a barrel attaching section having a barrel supporting section and a barrel pressing section, the barrel supporting section for contacting the syringe barrel so as to support the syringe barrel, the barrel pressing section for pressing the syringe barrel against the barrel supporting section and for releasing the syringe barrel from pressing against the barrel supporting section,
wherein the flange attaching operation section serves also as the barrel pressing section.

3. A syringe pump, comprising:
a flange attaching section having a flange supporting section and movable section, the flange supporting section being brought into pressure contact with a flange section of a barrel of a syringe so as to support the flange section, the movable section being capable of approaching the flange supporting section and separating therefrom due to rotational moving, the flange section being attached between the flange supporting section and the movable section;
a barrel attaching section having a barrel supporting section and a barrel pressing section, the barrel supporting section being brought into pressure contact with the barrel so as to support the barrel, the barrel pressing section pressing the barrel against the barrel supporting section and releasing the pressing; and
a differential section for instructing the barrel pressing section to execute the pressing after the approaching of the movable section is ended.

* * * * *